(12) United States Patent
Mansour

(10) Patent No.: US 8,298,196 B1
(45) Date of Patent: Oct. 30, 2012

(54) NEEDLELESS ACCESS CONNECTOR AND METHOD OF USE

(76) Inventor: George M. Mansour, Pomona, CA (US)

( * ) Notice: Subject to any disclaimer, the term of this patent is extended or adjusted under 35 U.S.C. 154(b) by 143 days.

(21) Appl. No.: 12/730,961

(22) Filed: Mar. 24, 2010

(51) Int. Cl.
*A61M 5/14* (2006.01)
(52) U.S. Cl. ...................................... 604/256
(58) Field of Classification Search .................. 604/246, 604/247, 249, 256; 251/149.1, 149.6, 149.7
See application file for complete search history.

(56) References Cited

U.S. PATENT DOCUMENTS

| | | | | |
|---|---|---|---|---|
| 5,746,414 | A * | 5/1998 | Weldon et al. | 251/149.6 |
| 5,788,215 | A * | 8/1998 | Ryan | 251/149.6 |
| 7,520,489 | B2 * | 4/2009 | Ruschke et al. | 251/149.7 |
| 8,038,123 | B2 * | 10/2011 | Ruschke et al. | 251/149.7 |
| 2003/0208165 | A1 * | 11/2003 | Christensen et al. | 604/256 |
| 2004/0124389 | A1 | 7/2004 | Phillips | |
| 2005/0121638 | A1 * | 6/2005 | Doyle | 251/149 |
| 2006/0027270 | A1 * | 2/2006 | Truitt et al. | 137/843 |
| 2006/0163515 | A1 * | 7/2006 | Ruschke | 251/149.7 |
| 2007/0218757 | A1 | 9/2007 | Guala | |
| 2010/0036330 | A1 * | 2/2010 | Plishka et al. | 604/256 |
| 2010/0063482 | A1 * | 3/2010 | Mansour et al. | 604/539 |
| 2010/0256573 | A1 * | 10/2010 | Mansour et al. | 604/256 |
| 2011/0028914 | A1 * | 2/2011 | Mansour et al. | 604/246 |

OTHER PUBLICATIONS

Max Plus Brochure, http://www.maximusmedical.com/pdf/maxPlus_Brochure.pdf (last accessed Jul. 29, 2009), 2 pages, Medegen, Inc.
Max Plus Clear Brochure, http://www.maximusmedical.com/pdf/MaxPlusClearNewFlyer.pdf (last accessed Jul. 29, 2009), 2 pages, Medegen, Inc.
Garcia, R. et al., "A Study of the Effects on Bacteremia and Sharps Injury Rates After Introduction of an Advanced Luer Activated Device (LAD) for Intravascular Access in a Large Hospital Setting," http://www.maximusmedical.com/pdf/Garciac%20Study.pdf (last accessed Jul. 29, 2009), 6 pages, Medegen, Inc.
U.S. Appl. No. 12/551,069, Truitt et al.
U.S. Appl. No. 12/619,598, Truitt et al.

* cited by examiner

*Primary Examiner* — Nicholas Lucchesi
*Assistant Examiner* — Aarti B Berdichevsky
(74) *Attorney, Agent, or Firm* — McDermott Will & Emery LLP

(57) ABSTRACT

A positive-displacement needleless access connector includes a housing with a female luer fitting, a base with a male luer fitting, and a valve element with a proximal end that creates a seal in the housing, a septum, and a distal end that fastens to the base to vent the septum; the base and the valve element coupling to each other to create an assembly that has a greatest outer diameter smaller than an inner diameter of the housing.

4 Claims, 8 Drawing Sheets

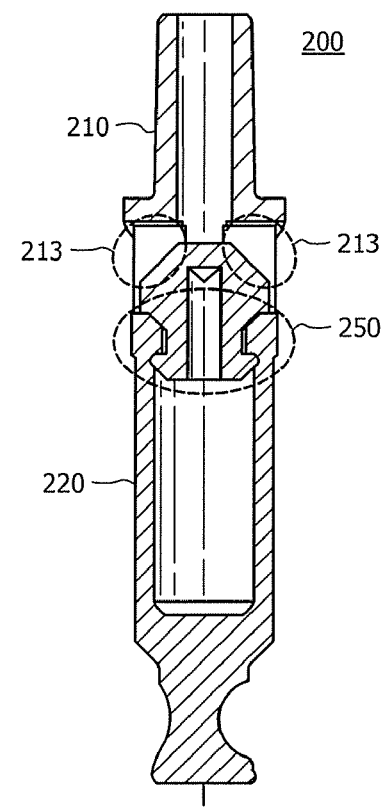
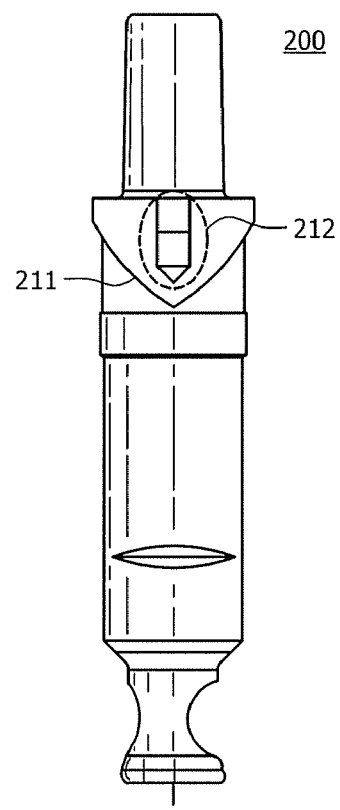
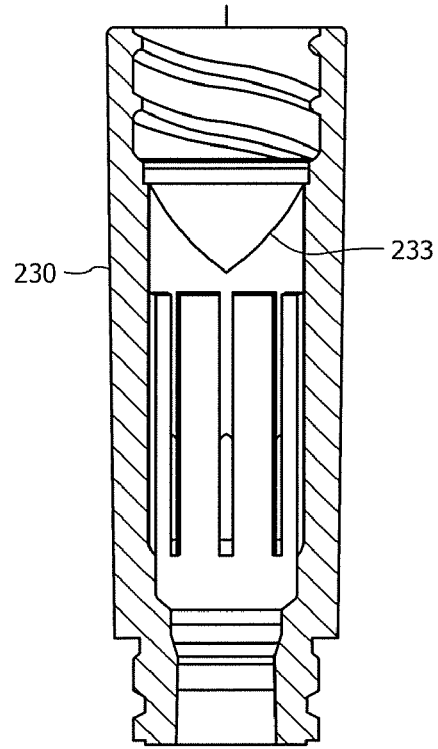
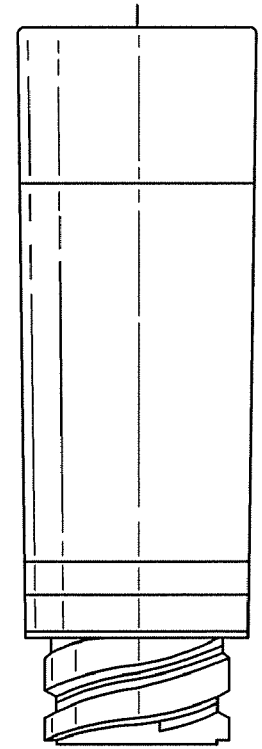
FIG. 3A
FIG. 3B

800

801 — FASTENING A DISTAL END OF THE VALVE ELEMENT TO A PROXIMAL END OF THE BASE, CREATING A SEAL BETWEEN THE VALVE ELEMENT AND THE BASE SEPARATING THE SEPTUM FROM A FLUID FLOW PATH BETWEEN THE FIRST AND SECOND LUER FITTINGS

802 — DISPOSING THE VALVE ELEMENT AND THE BASE WITHIN THE HOUSING

803 — PERMANENTLY AFFIXING THE BASE TO THE HOUSING

*FIG. 8*

NEEDLELESS ACCESS CONNECTOR AND METHOD OF USE

TECHNICAL FIELD

This disclosure relates to needleless access connectors and more particularly to positive displacement needleless access connectors.

BACKGROUND

Modern medical treatment often requires medical professionals to introduce fluids into a patient or withdraw fluids from a patient. For example, a patient may need treatment that requires a medical professional to withdraw urine or blood from the urethra or a vein, respectively. Conversely, the medical professional may need to introduce drugs or nutrients into the patient's vein (i.e., intravenously). To create a path for the flow of fluid into or from the patient, one method requires that the medical practitioner use a catheter where one end of the catheter is inserted into the patient. The other end of the catheter connects to an intravenous bag (IV bag), through an IV line. Needleless access connectors employ valves that allow a medical practitioner to remove or add devices (e.g., IV bags) to the catheter without the use of a needle. An example of a needleless access connector is shown in FIGS. 1A and 1B.

FIG. 1A is a cut-away view of a current needleless access connector 100. Needleless access connector 100 includes housing 120, which has female luer fitting 101 at the proximal end, base 130, which has male luer fitting 102 at the distal end, and valve element 103, which sits inside housing 120 and on top of base 130. Housing 120 and base 130 are made from rigid plastic, usually polycarbonate, and the valve element 103 is made from liquid silicone so it is elastic and collapses. When in use, male luer fitting 102 is connected to, e.g., a catheter or to a female luer, and female luer fitting 101 is connected to a fluid reservoir, e.g., an IV bag or male luer. Female luer fitting 101 is connected to the fluid reservoir via a second male luer fitting 106, which has a hollow member (as shown in FIG. 1B) and is inserted through the top of female luer fitting 101. The insertion of male luer 106 collapses valve element 103 down into volume 104 to break the seal and create a fluid flow path. FIG. 1B shows collapsible valve element 103 in the collapsed position after insertion of male luer 106 into female luer 101. Male luer 106 delivers fluid, e.g., from an IV bag, which flows around valve element 103 into channels in male luer fitting 102 and into the catheter or female luer.

Inside valve element 103 is a gap (or septum, not shown), that is filled with air. Needleless access connector 100 is a positive displacement device, so that when a new connection is made at female luer fitting 101, device 100 pulls fluid in from the male side of the valve (i.e., the side proximate male luer fitting 102). When a disconnection is made at female luer fitting 101, device 100 pushes fluid in from the female side (i.e., the side proximate the top of female luer fitting 101). The advantage of positive displacement is that when a disconnection is made, device 100 expels fluid out of the male luer fitting 102 and effectively flushes the catheter. By contrast, some devices on the market today have negative displacement, so that when a male luer (e.g., male luer 106) is disconnected, such devices pull a small amount of liquid from the male luer 102 side. When liquid is pulled from the male luer 102 side of a catheter that is attached to the vein of a patient, blood could be pulled into the catheter lumen and if this blood is left in the catheter lumen it may clot and cause health problems for the patient. Positive displacement connectors avoid this problem by pushing fluid out when a male luer (e.g., male luer 106) is disconnected from the needleless access connector and its collapsible valve moves from its collapsed state to its uncollapsed state. The purging of fluid, from positive displacement connectors, helps to prevent blood from entering the tip of the catheter, thereby preventing blood clotting/contamination and thus, bloodstream infections.

In operation, when the female end of needleless access connector 100 is accessed by a male luer (FIG. 1B), valve element 103 is sufficiently elastic so that it can bend out of the way to allow flow and then return to its original shape after a disconnection is made at the female end. Thus, needleless access connector 100 re-seals itself and forms a flat surface that can be disinfected at the top surface 110 using an alcohol swab.

Before needleless access connector 100 is used to connect a device to, for example, a catheter, needleless access connector 100 will contain some air. This air is removed before using needleless access connector 100 with a catheter because otherwise it may be pumped into the patient causing harm to the patient. Usually, to remove this air, the medical practitioner inverts the needleless access connector and attaches a syringe containing saline to the needleless access connector. The saline is then pushed through the needleless access connector, thereby expelling the air from the connector. (This process is known as priming, and the minimum volume of liquid required to remove all the air from the needleless access connector is known as the priming volume.) Some medical practitioners prefer needleless access connectors with smaller priming volumes to reduce delay in medication delivery.

After a needleless access connector is primed, the medical practitioner usually connects the male end 102 to a catheter (not shown) The medical practitioner connects a male luer from the IV bag (not shown) to the needleless access connector. For example, a medical practitioner would connect the end of syringe 106 to female luer fitting 101, as shown in FIG. 1B.

Of note in needleless access connector 100 is the shapes of housing 120, base 130, and valve element 103. Valve element 103 has flange 105, which is a portion with an outer diameter greater than that of the body of the valve element 103. Housing 120 has shoulder 107, which conforms to flange 105. When assembled, flange 105 is held securely between base 130 and shoulder 107, thereby creating a seal between flange 105 and base 130. The reason for the seal is so that the air in the septum can be vented out without the air getting into the fluid flow path from male luer 106 to male luer 102. Although not shown herein, there are two vent holes in the y-axis direction that extend from the threaded portion of base 130 to the septum of valve element 103 that allow air out of and into, the septum as valve element 103 is compressed and uncompressed without mixing with the fluid. Once assembled, housing 120 and base 130 are welded at interface 115.

Flange 105 increases the overall width of valve element 103, and connector 100 allows the fluid to flow around flange 105, thereby making connector 100 itself wide. As a result, connector 100 can look big when compared to a catheter (not shown) and especially when connector 100 is placed against the skin of a neonate. Typical use of connector 100 is to tape the catheter to a patient's skin near the point where the catheter couples to connector 100. However, the wide shape of connector 100 may cause connector 100 to fit uncomfortably against the skin. Additionally, the width of connector 100 can make for a large priming volume.

BRIEF SUMMARY

Various embodiments include a connector with a valve element that fastens to the base. For instance, in one embodiment, an example valve element is flush with the base where the two components mate. In another example, the base and the valve element couple to each other to create an assembly that has a greatest outer diameter that is smaller than an inner diameter of the housing.

Various embodiments minimize or eliminate the flange so that the width profile of the valve element, and the connector as a whole, can be reduced when compared to the prior solutions shown in FIGS. 1A and 1B. An example technique for eliminating the flange and fastening the valve element to the base includes using a snap fitting that mates the valve element to the base, though other embodiments can use other techniques. Additional embodiments include methods of manufacturing a connector.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which:

FIGS. 3A and 3B provide an exploded illustration of the exemplary positive displacement needleless access connector, adapted according to one embodiment of the invention.

FIG. 8 is an illustration of an exemplary method for manufacturing a positive displacement needleless connector according to one embodiment.

DETAILED DESCRIPTION

Figures 2A, 2B:
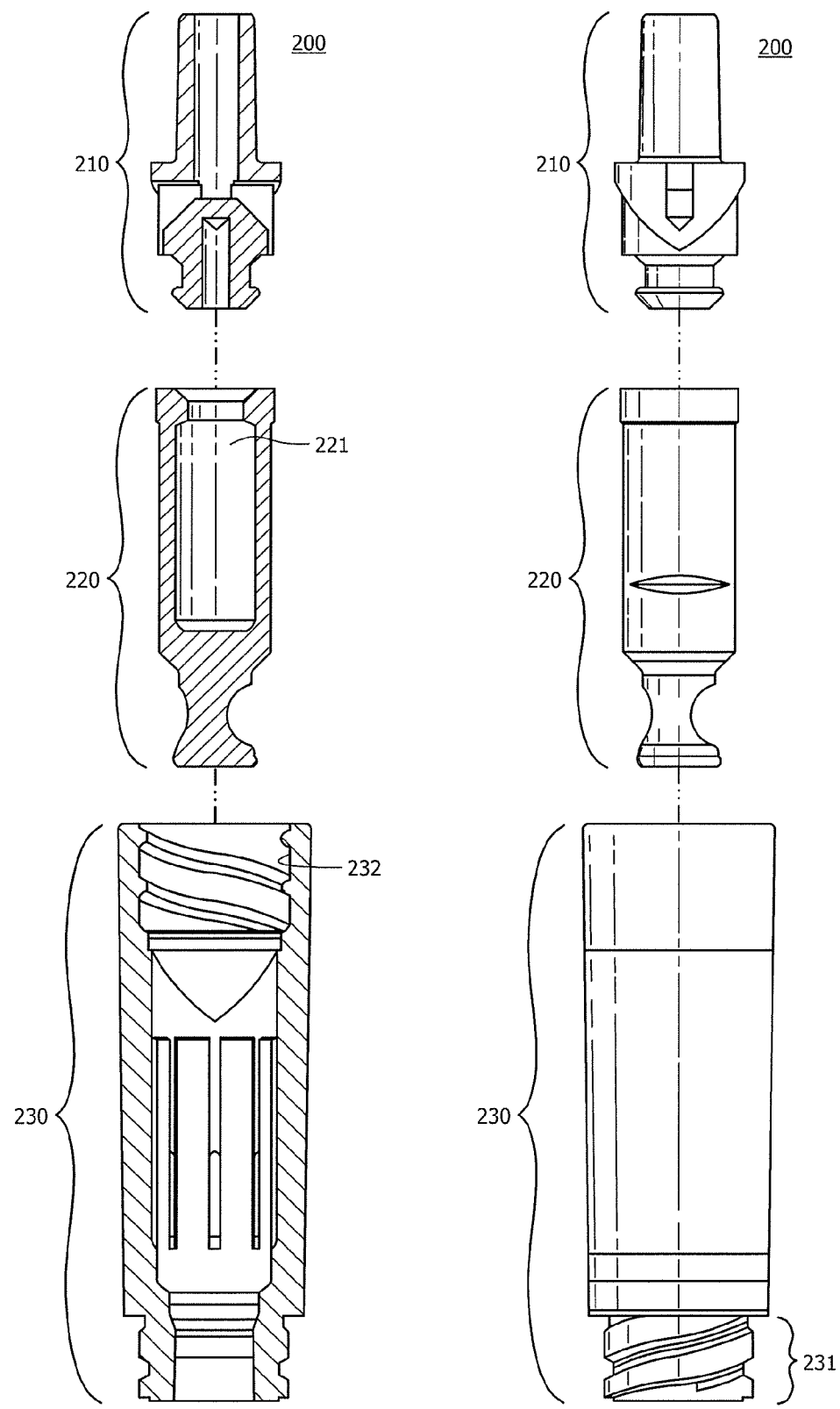
FIGS. 2A and 2B provide an exploded illustration of an exemplary positive displacement needleless access connector, adapted according to one embodiment of the invention.

FIGS. 2A and 2B provide an exploded illustration of exemplary positive displacement needleless access connector 200, adapted according to one embodiment of the invention. FIG. 2A is a cut-away view, whereas FIG. 2B shows the exterior of connector 200.

Connector 200 has three basic parts—base 210, valve element 220, and housing 230. Housing 230 has female luer fitting 231 at the proximal end, which connects, for example, to a fluid reservoir, such as an IV bag. Base 210 and threads 232 form a male luer fitting at the distal end of connector 200, the male luer fitting connecting to, for example, a catheter that is in communication with a patient. Valve element 220 includes septum 221, which is filled with air and vents to the atmosphere as it is compressed and uncompressed, as explained in more detail below.

FIGS. 3A and 3B provide an exploded illustration of exemplary positive displacement needleless access connector 200, adapted according to one embodiment of the invention. FIG. 3A is a cut-away view, whereas FIG. 3B shows the exterior of connector 200, and both FIGS. 3A and 3B show base 210 fastened to valve element 220.

Base 210 and valve element 220 are coupled together using, in this embodiment, an interlocking male/female fitting 250, referred to herein for convenience as a snap fitting. The top of valve element 220 that is the female part of the snap fitting 250 is made small enough so that is has a tight, sealing squeeze at the corresponding portion of base 210 that forms the male portion of snap fitting 250. In many embodiments, the seal at the snap fitting 250 is airtight, at least at normal operating temperatures and pressures, in order to keep the air separate from the fluid in connector 200. During manufacturing, base 210 and valve element 220 can be fastened together by forcing them together, either by hand or by machine. In some embodiments, about a pound of force is sufficient to make the connection, and about two pounds is sufficient to break the connection, though various embodiments may differ.

While FIGS. 3A and B show a snap fitting 250, the scope of embodiments is not so limited. For instance, other embodiments may employ different types of fastening fittings, such as threaded assemblies or other fittings.

Figure 1A:
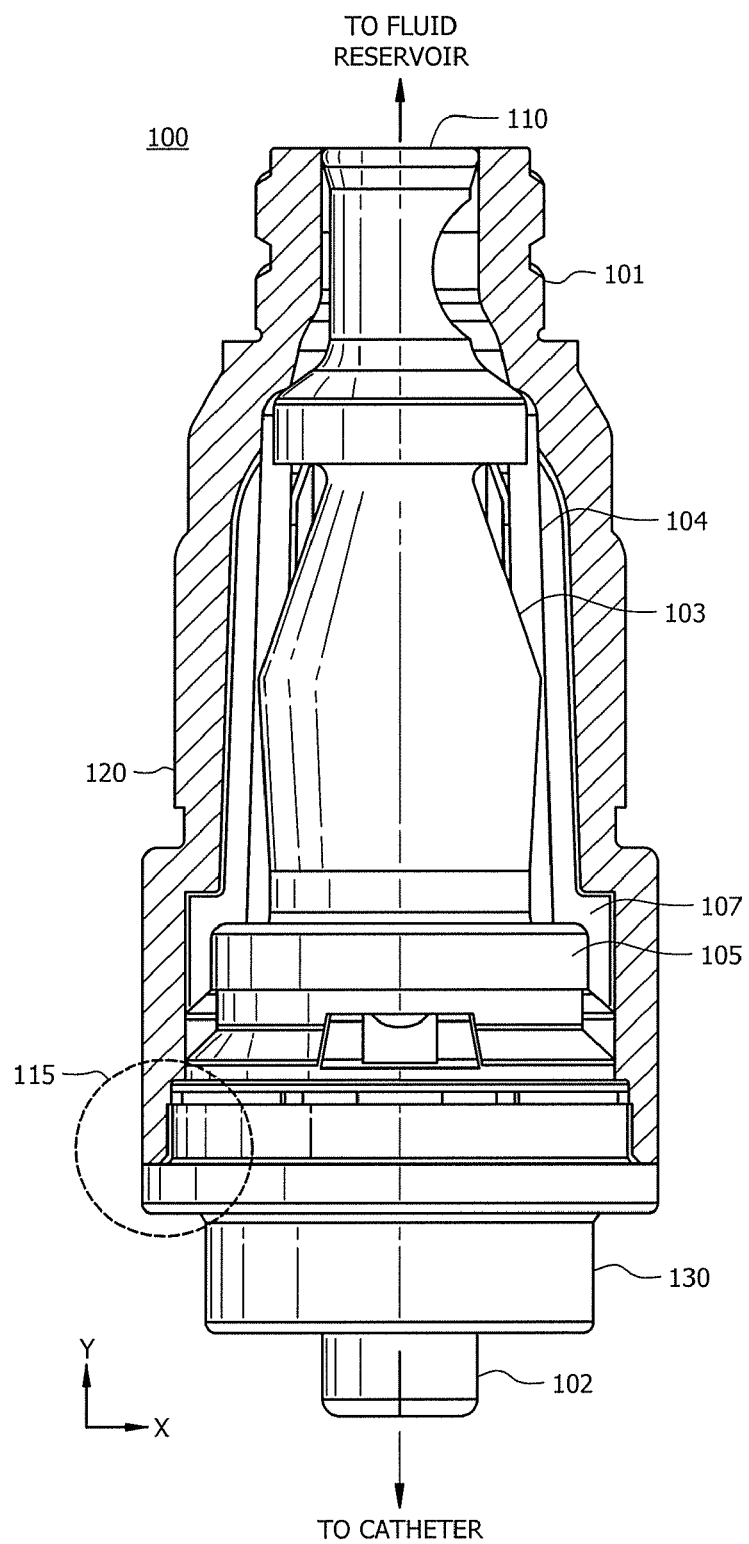
FIG. 1A is a cut-away view of a current needleless access connector.

In the exemplary embodiment of FIGS. 3A and 3B, the outside surfaces of base 210 and valve element 220 are flush at snap fitting 250. For real-world devices it is understood that the outside surfaces of valve element 220 and base 210 will rarely be exactly flush, but some amount of tolerance (e.g., about 2%) is acceptable in some embodiments. Thus, connector 200 replaces the flange of conventional positive displacement devices (e.g., flange 105 of FIG. 1A) with the snap fitting 250 and flush outer surface shown in FIGS. 3A and 3B. The shape of valve element 220, therefore, has a narrower profile, and can be used in narrower-profile connectors.

Base 210 and valve element 220 fasten together to form an assembly that is placed into housing 230. Connector 200 uses a somewhat "v"-shaped fitting to mate base 210 to housing 230. Complementary surfaces 211 and 233 are basically v-shaped but have slight curvature and fit together to hold base 210 in place when base 210 is inserted into housing 230. As base 210 is inserted, the complementary surfaces 211, 233 self-correct the alignment of base 210 with respect to housing 230, acting like a cam. Thus, if base 210 is inserted some arbitrary number of degrees out of alignment, complementary surfaces 211, 233 (once contacted) rotate base 210 into place. As a result, base 210 sits precisely, and after the weld is made, air vents 212 will be able to vent to the atmosphere while distal flow channels 213 are connected to the male luer outlet of base 210.

Distal flow channels 213 and air vents 212 are perpendicular to each other in this embodiment. Thus, one of two air vents 212 is shown in FIG. 3B, whereas distal flow channels 213 are shown in cross-section in FIG. 3A. Flow and venting are shown in more detail in FIG. 4.

Figure 4:
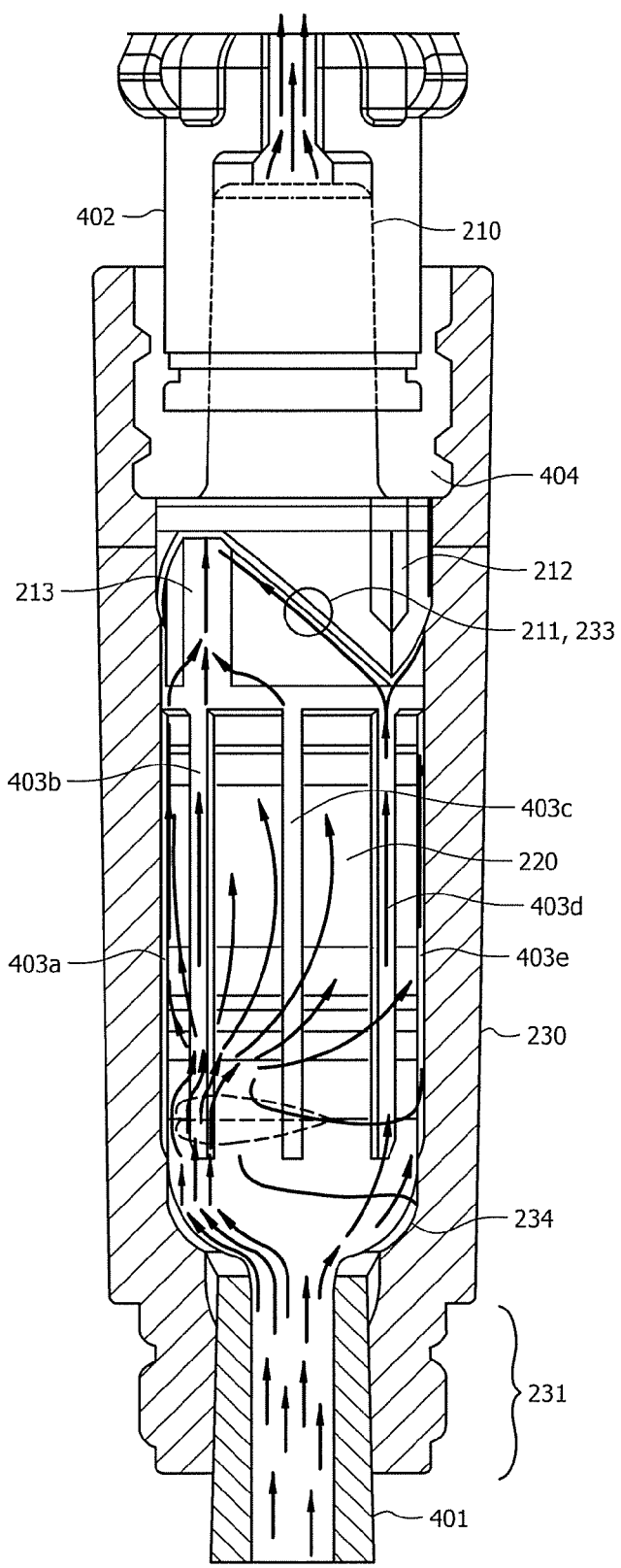
FIG. 4 is a see-through illustration of the exemplary connector in use, according to one embodiment.

FIG. 4 is a see-through illustration of exemplary connector 200 in use, according to one embodiment. In FIG. 4, fluid is being transferred from male luer connector 410, which is engaged with female luer fitting 231, through housing 230, through the male luer outlet of base 210 and into female luer fitting 402. Such an example may include transferring fluid from an IV bag (not shown) into a patient's bloodstream. While FIG. 4 shows flow into a patient, it is understood that various embodiments of the invention also facilitate flow of fluids from a patient.

When there is no connection at the female luer fitting 231, valve element 230 creates a seal at the proximal end of female luer fitting 231 as well as at shoulder 234. Such seal prevents the flow of fluids through connector 200 when not in use. Also, the seal at the proximal end of fitting 231 creates a flush surface that is swabbable. The seals at the proximal end of female luer fitting 231 and at shoulder 234 are shown in FIG. 5.

During use, male luer fitting 401 collapses valve element 220 and breaks the seals at shoulder 234 and at the proximal end of fitting 231. Fluid is then free to flow around valve element 230 and through housing 230 via proximal flow channels 403, which are formed into the inner surface of housing 230. The weld at surfaces 211, 233 stops the fluid so that the fluid flows around the v-shape and into the distal flow channels 213, where the fluid is directed out through the male luer outlet of base 210. Air from septum 221 is vented to the atmosphere through air vents 212 and into threaded chamber 404, which is part of the male luer fitting formed by base 210 and housing 230. The air passageway is defined by vent 212 and the inner surface of housing 230, and the weld at surfaces 211, 233 creates a seal that keeps the air flow separate from the fluid flow. The threaded chamber 404 is not airtight, even when engaged with female fitting 402, thereby allowing septum 221 to communicate with the ambient atmosphere as valve element 220 is compressed, as in FIG. 4, or uncompressed.

Figures 5, 6:
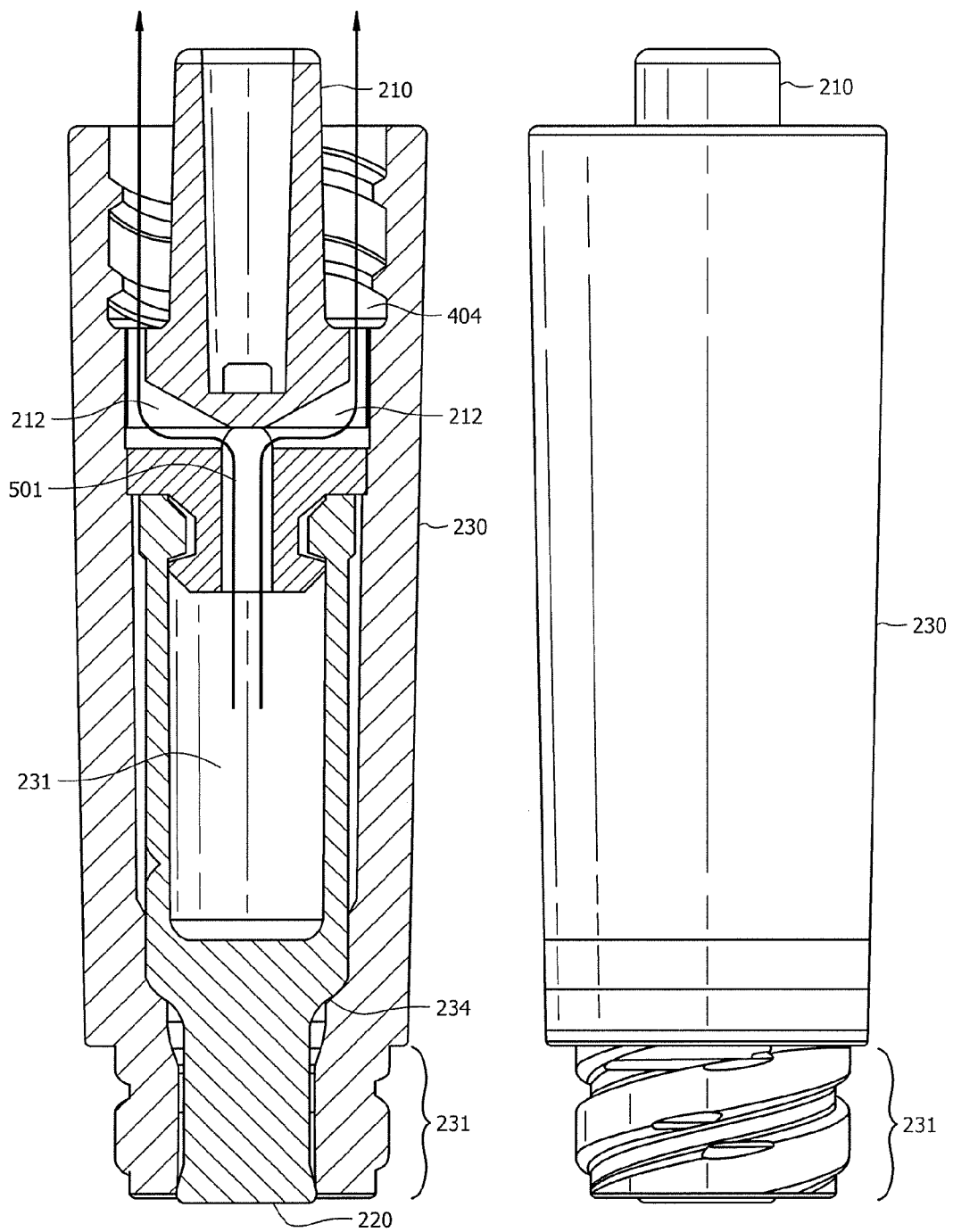
FIG. 5 is a cross-section illustration of the exemplary connector, adapted according to one embodiment, which is ninety degrees rotated from the cross-sections of FIGS. 2A, B and 3A, B.
FIG. 6 is an illustration of the exemplary connector assembled and ready for use, according to one embodiment.

FIG. 5 is a cross-section illustration of exemplary connector 200, adapted according to one embodiment, which is ninety degrees rotated from the cross-sections of FIGS. 2A, B and 3A, B. Of note in FIG. 5 is the air passageway from septum 221 to the atmosphere. The air passageway includes single vent 501, formed in base 210, and vents 212. The single vent 501 and the vents 212 form a substantially "Y"-shaped air passageway. This is in contrast to prior designs (not shown) that include two or more separate vents, formed in the y-axis direction ("axially"), directly connecting the atmosphere to the septum.

During conventional manufacturing techniques, an injection molding technique is used, and the two or more separate vents are created using long, thin pins inserted into the mold cavity when the material is hot. When the mold is opened, the long, thin pins are removed to form the two or more separate vents. However, long, thin pins have a tendency to break during use. The general rule is that shorter and thicker pins last longer.

By contrast, base 210 has relatively wide and short vents 212 that can be formed by correspondingly-shaped metal pieces in the mold. The air passageway has a triangular broadening in each vent 212 from the center axis to the outer surface of base 210. The correspondingly-shaped metal pieces (not shown) are thicker and shorter than the long, thin pins of conventional techniques and are, therefore, less subject to breaking. Single channel 501 is made relatively wide, and it is placed in the portion of base 210 that corresponds to the male portion of snap fitting 250. Furthermore, since single channel 501 does not have to traverse the full length from septum 221 to threaded chamber 404, it avoids cramping the fluid flow path. Accordingly, single channel 501 is not made with a long, thin pin either.

FIG. 6 is an illustration of exemplary connector 200 assembled and ready for use, according to one embodiment. Housing 230 may be made of material including polycarbonate, polystyrene and acrylonitrile butadiene styrene. Housing 230 includes female luer fitting 231, which, in some embodiments, meets ISO standard 594. Similarly, the configurations of the male luer at the distal end of housing 230 and formed with base 210, in some embodiments, meets ISO standard 594. Valve element 220 is disposed within housing 230 and may be made of elastic material such as silicone rubber, which is deformable and biocompatible.

Figure 7:
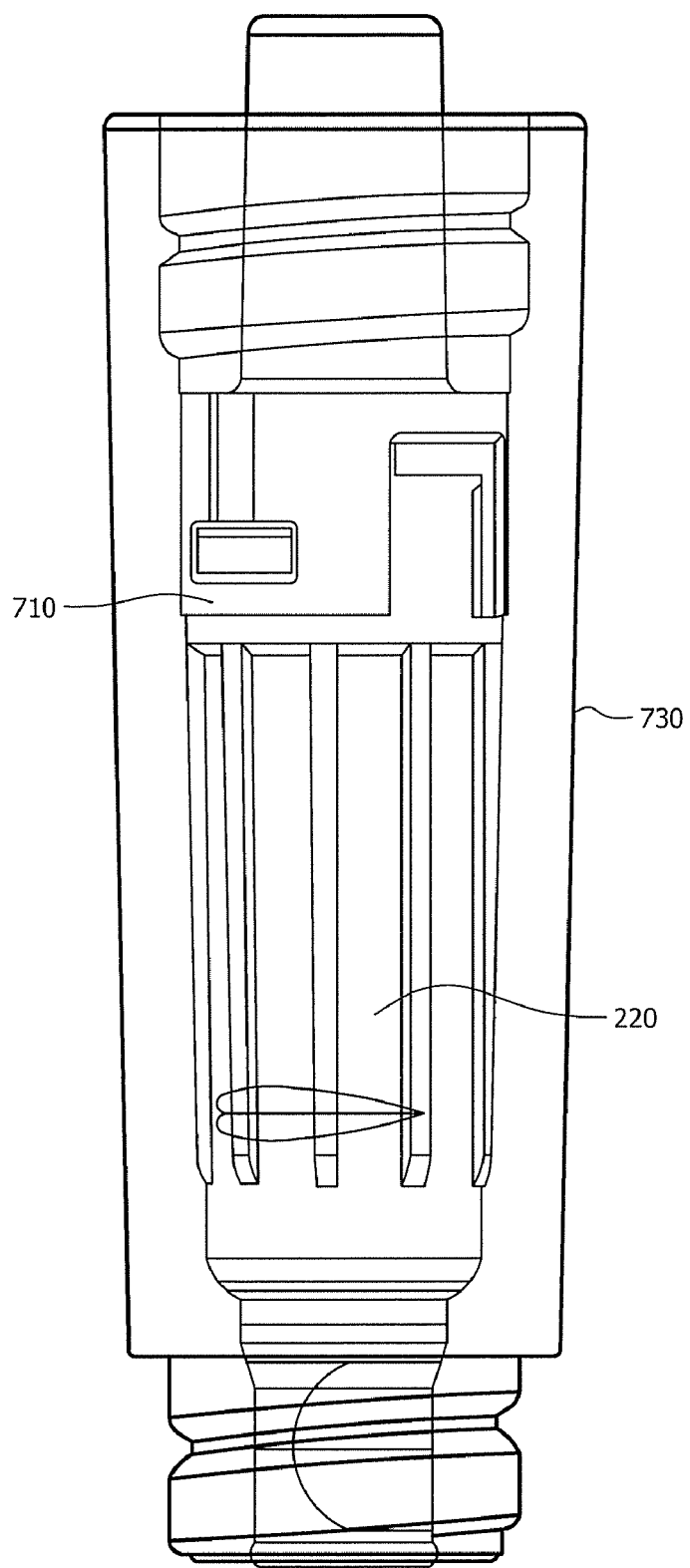
FIG. 7 is an illustration of an exemplary connector, adapted according to one embodiment.

FIG. 7 is an illustration of exemplary connector 700, adapted according to one embodiment. Connector 700 is similar to connector 200 (e.g., FIGS. 2-6) but uses a slot and key fitting to mate housing 730 to base 710, instead of the v-shaped fitting featured in connector 200. In a slot and key configuration, base 710 has a protrusion (key) that is sized to fit into a slot in the inner surface of housing 730 (or vise versa). During manufacture, base 710 and valve element 220 are inserted into housing 730 and turned it until the slot mates with the key. Base 710 and housing 730 are then welded. The scope of embodiments is not limited to a slot and key fitting or a v-shaped fitting, as any of a variety of techniques for mating a base and a housing can be used in a variety of embodiments.

FIG. 8 is an illustration of exemplary method 800 for manufacturing a positive displacement needleless connector according to one embodiment. Method 800 may be performed, for example, by a human and/or one or more machines.

In block 801, a distal end of the valve element is fastened to a proximal end of the base. The fastening creates a seal between the valve element and the base separating the septum from a fluid flow path between the first and second luer fittings. Block 801 creates an assembly, such as that shown in FIG. 3A, which includes a valve element and a base mated together. In one example, the valve element and base are mated using a snap fitting, though other fastening techniques can be used in other embodiments.

In block 802, the valve element and the base are disposed within the housing. For instance, a v-shaped fitting can be used, such as that shown in FIGS. 3A and 3B, that self-aligns the base and housing, though other fittings, such as a key and slot and can be used. When the valve and base are disposed within the housing, the proximal end of the valve element creates one or more seals at the proximal end of the housing.

In block 803, the base and housing are permanently affixed. Various techniques can be used in block 803, such as ultrasonic welding, applying adhesives, and the like. In this example, the base and housing fit together tightly so that a seal is created that separates air venting paths from fluid flow paths after the base and housing are permanently affixed.

Various embodiments are not limited to the process shown in FIG. 8, as various actions may be added, omitted, rearranged, or modified.

Figure 1B:
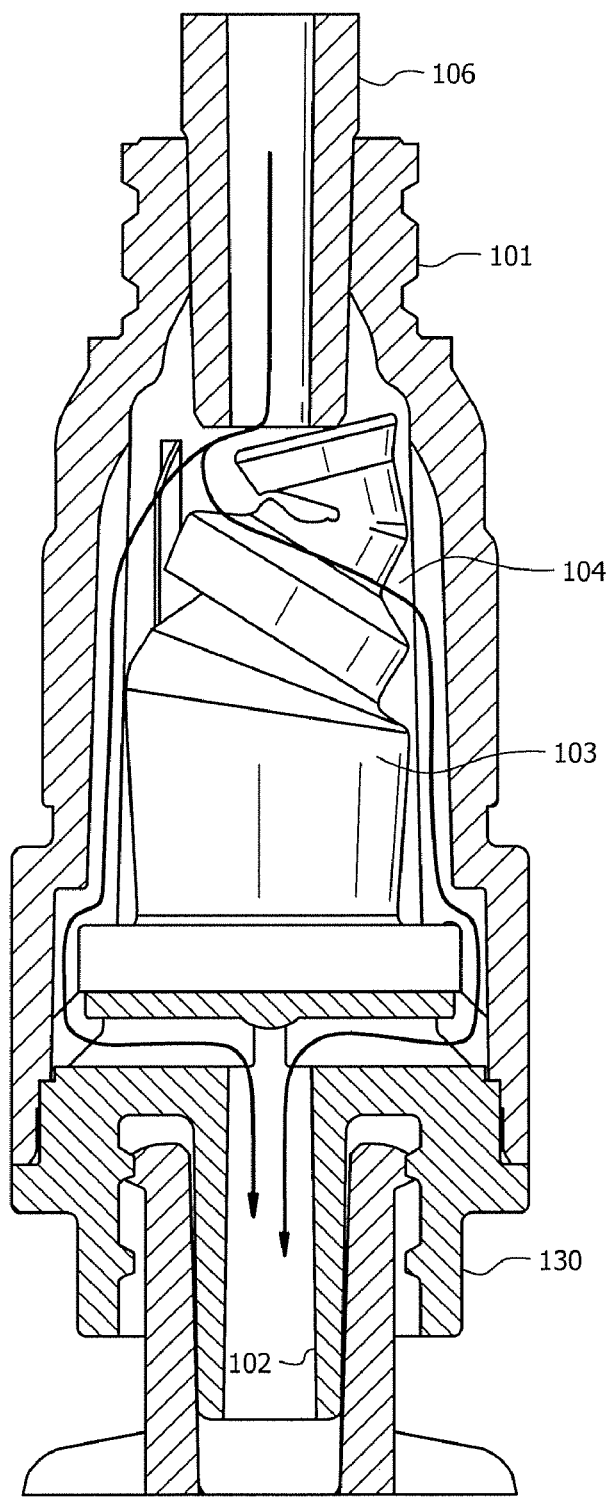
FIG. 1B shows a collapsible valve element in the collapsed position after insertion of a male luer into a female luer.

Some embodiments may enjoy one or more advantages over prior solutions. In one aspect, elimination of the flange of FIGS. 1A and 1B decreases the size of the valve element and, in turn, the connector as a whole. A connector with a smaller volume is generally expected to have a smaller priming volume, as well, which may reduce fluid and waste and may be more visually appealing to health care professionals. Additionally, some embodiments have a reduced overall width, which is generally more comfortable to a patient when catheter is taped to the skin close to the connector.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A positive-displacement needleless access connector comprising:
    a housing with a female luer fitting;
    a base with a male luer fitting; and
    a valve element with a proximal end that creates a seal in the housing, a septum, and a distal end that fastens to the base to vent the septum, the base and the valve element coupling to each other to create an assembly that has a greatest outer diameter that is smaller than an inner diameter of the housing;
    wherein the base comprises a "Y"-shaped vent path from the septum to a distal end of the base, the "Y"-shaped vent path comprising triangularly shaped branches.

2. The positive-displacement needleless access connector of claim 1 in which the distal end of the valve element fastens to the base using a snapping mechanism.

3. The positive-displacement needleless access connector of claim 1 in which the housing is coupled to the base using a "v"-shaped fitting.

4. The positive-displacement needleless access connector of claim 1 in which the housing is coupled to the base using a key and slot fitting.

* * * * *